US008263099B2

(12) United States Patent
Otsubo et al.

(10) Patent No.: US 8,263,099 B2
(45) Date of Patent: Sep. 11, 2012

(54) INSECT GROWTH REGULATING COMPOSITION

(75) Inventors: Toshiro Otsubo, Sanda (JP); Shoji Maruyama, Tokushima (JP); Yoshihiro Takebayashi, Toyonaka (JP); Kousei Kuroda, Kakogawa (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 92 days.

(21) Appl. No.: 12/429,019

(22) Filed: Apr. 23, 2009

(65) Prior Publication Data

US 2009/0246239 A1  Oct. 1, 2009

Related U.S. Application Data

(62) Division of application No. 11/067,728, filed on Mar. 1, 2005, now abandoned.

(30) Foreign Application Priority Data

Mar. 1, 2004 (JP) .................................. 2004-055835

(51) Int. Cl.
 *A01N 25/34* (2006.01)
 *A01N 25/26* (2006.01)
(52) U.S. Cl. ....................................... 424/408; 504/100
(58) Field of Classification Search .................. None
 See application file for complete search history.

(56) References Cited

U.S. PATENT DOCUMENTS

| | | | |
|---|---|---|---|
| 4,853,223 A | 8/1989 | Graf et al. | |
| 4,889,719 A * | 12/1989 | Ohtsubo et al. | 424/408 |
| 4,900,551 A * | 2/1990 | Ohtsubo et al. | 424/408 |
| 5,063,059 A * | 11/1991 | Ohtsubo et al. | 424/408 |
| 5,178,872 A * | 1/1993 | Ohtsubo et al. | 424/408 |
| 5,300,293 A * | 4/1994 | Minagawa et al. | 424/405 |
| 5,306,499 A * | 4/1994 | Ohtsubo et al. | 424/405 |
| 5,488,043 A * | 1/1996 | Yamada et al. | 514/120 |
| 5,698,540 A * | 12/1997 | Katayama et al. | 514/120 |
| 5,707,639 A * | 1/1998 | Owaga et al. | 424/409 |
| 5,929,053 A * | 7/1999 | Murakami et al. | 514/89 |
| 6,337,130 B1 | 1/2002 | Van Koppenhagen et al. | |
| 6,905,699 B2 | 6/2005 | Nakamura | |
| 2004/0120976 A1 | 6/2004 | Inui et al. | |

FOREIGN PATENT DOCUMENTS

| | | |
|---|---|---|
| EP | 0 148 769 A1 | 7/1985 |
| EP | 0 267 150 A1 | 5/1988 |
| EP | 0 313 089 A2 | 4/1989 |
| EP | 0 322 820 A1 | 7/1989 |
| EP | 0 611 253 A1 | 8/1994 |
| GB | 2 187 957 A | 9/1987 |
| JP | 58-144304 A | 8/1983 |
| JP | 61-33230 A | 2/1986 |
| JP | 2939302 | 6/1999 |
| JP | 2002-80311 A | 3/2002 |
| JP | 2003-40706 A | 2/2003 |
| WO | 97/18705 A2 | 5/1997 |
| WO | 97/34478 A1 | 9/1997 |
| WO | 97/44125 A1 | 11/1997 |
| WO | 03/005116 A1 | 6/2003 |
| WO | 03/051116 A1 | 6/2003 |

OTHER PUBLICATIONS

Hashemi et al., (Iranian Polymer Journal, 10(4), 265-270, 2001). Encapsulation process in synthesizing polyurea microcapsules containing pesticide.*
Australian Office Action issued on Nov. 5, 2009 from the Australian Patent Office in a counterpart Australian application (Application No. 2005200701).
Insecticide Formulation Guide, Japan Plant Protection Association, Oct. 30, 1997. pp. 65-68.
Liliana Schwartz et al., "Controlled-Release Systems for the Delivery of Cyromazine into Water Surface," Journal of Agricultural and Food Chemistry, 2003, vol. 51, pp. 5972-5976.
Notice of Proposed and Final Decisions and Directors Finding, vol. 99, No. 10, Apr. 6, 1999, XP-002344991, pp. 1-11.
Liliana Schwartz et al., "Controlled-Release Systems for the Insect Growth regulator Pyriproxyfen," Journal of Agricultural and Food Chemistry, vol. 51, No. 20, Sep. 24, 2003, XP-002344990, pp. 5985-5989.
B.H. Thompson et al., "Laboratory and Field Trials Using Altosid® Insect Growth Regulator Against Black Flies (Diptera: Simuliidae) of Newfoundland, Canada", J. Med. Entomol., vol. 16, No. 6, Dec. 18, 1979, XP-009053892, pp. 536-546.

* cited by examiner

*Primary Examiner* — David J Blanchard
*Assistant Examiner* — Tigabu Kassa
(74) *Attorney, Agent, or Firm* — Sughrue Mion, PLLC

(57) ABSTRACT

A microencapsulated insect growth regulating composition comprising an insect growth regulation active ingredient in a wall formed of polyurethane or polyurea, having an average particle diameter of 1 to 40 μm, a wall thickness of 0.005 to 0.5 μm, a ratio of a wall thickness/an average particle diameter of 0.0003 to 0.003, and a volume ratio of microencapsulated particles having a particle diameter of not less than 50 μm of not more than 20% by volume based on a total volume of microencapsulated particles sufficiently exerts efficacy of the active ingredient, i.e., the insect growth regulation activity.

3 Claims, No Drawings

INSECT GROWTH REGULATING COMPOSITION

CROSS REFERENCE TO RELATED APPLICATION

This is a divisional of application Ser. No. 11/067,728 filed Mar. 1, 2005 now abandoned, which claims benefit of priority based on Japanese Application No. 2004-055835, filed Mar. 1, 2004. The entire disclosure of the prior applications is hereby incorporated by reference.

BACKGROUND OF THE INVENTION

1. Field of the Invention

The present invention relates to a microencapsulated insect growth regulating composition.

2. Prior Art

A poisonous bait composition in which an insect growth regulating active ingredient is microencapsulated is known in U.S. Pat. No. 5,300,293.

The composition has not sufficient efficacy when used in agricultural fields, apart from a poisonous bait of a cockroach.

SUMMARY OF THE INVENTION

The present invention provides a microencapsulated insect growth regulating composition comprising an insect growth regulating active ingredient, wherein efficacy of the insect growth regulating active ingredient as an active ingredient is sufficiently exerted, particularly, in agricultural fields.

In order to achieve this object, the present invention makes efficacy of an insect growth regulation active ingredient to be sufficiently exerted by adopting an average particle diameter, a wall thickness, a ratio of wall thickness/average particle diameter of microcapsules, and a volume ratio of microcapsule particles of 50 μm or larger in a specified range.

That is, the present invention is:

1. A microencapsulated insect growth regulating composition, which comprises an insect growth regulating active ingredient encapsulated in a wall formed of polyurethane or polyurea, having an average particle diameter of 1 to 40 μm, a wall thickness of 0.005 to 0.5 μm, and a ratio of wall thickness/average particle diameter of 0.0003 to 0.003, wherein a volume ratio of microencapsulated particles having a particle diameter of not less than 50 μm is not more than 20% by volume based on a total volume of microcapsule particles.

2. The insect growth regulating composition according to 1, wherein the insect growth regulating active ingredient is an insect juvenile hormone-like compound.

3. The insect growth regulating composition according to 1, wherein the insect growth regulating active ingredient is 4-phenoxyphenyl 2-(2-pyridyloxy)propyl ether.

4. Use of an insect growth regulating composition according to any one of 1 to 3 for controlling an insect pest.

5. A method for controlling an insect pest comprising applying an effective amount of an insect growth regulating composition according to any one of 1 to 3 directly to an insect pest or to a place where an insect pest inhabits.

DETAILED DESCRIPTION OF THE INVENTION

The insect growth regulating composition of the present invention is characterized by a microencapsulated insect growth regulating composition, which comprises an insect growth regulating active ingredient encapsulated in a wall formed of a polyurethane or a polyurea, having an average particle diameter of 1 to 40 μm, a wall thickness of 0.005 to 0.5 μm, and a ratio of wall thickness/average particle diameter of 0.0003 to 0.003, wherein a volume ratio of microencapsulated particles having a particle diameter of not less than 50 μm is not more than 20% by volume based on a total volume of microcapsule particles.

The insect growth regulating composition of the present invention can be prepared, for example, by the following method.

First, an insect growth regulating ingredient and a polyvalent isocyanate are mixed to obtain an oil phase. At this time, a hydrophobic oil solvent may be added to the organic phase, if necessary. The resulting oil phase is dispersed by mixing with an aqueous phase containing a dispersant (dispersing step), and a polyhydric alcohol or a polyvalent amine is added to the dispersion, to perform a microcapsule forming reaction (microencapsulating reaction step). The reaction temperature of this microencapsulating reaction step is usually in a range of 20 to 85° C., and the reaction time is usually in a range of 1 to 90 hours.

In the aforementioned microencapsulating reaction step, when a polyhydric alcohol is used, a microencapsulated product having a polyurethane wall is obtained and, when a polyvalent amine is used, a microencapsulated product having a polyurea wall is obtained.

When a microencapsulating reaction step is performed using a polyhydric alcohol, an oil phase may be dispersed in an aqueous phase in which the polyhydric alcohol is mixed, in place of dispersing an oil phase into an aqueous phase, and then adding the polyhydric alcohol.

Alternatively, a microencapsulating reaction step may be performed without adding a polyhydric alcohol or a polyvalent amine. In this case, a microencapsulated product having a polyurea wall is obtained.

Examples of the dispersant used in the aforementioned process include water-soluble polymers, and specific examples thereof include natural polysaccharides such as gum arabic, natural water-soluble polymers such as gelatin and collagen, water-soluble semi-synthetic polysaccharides such as carboxymethylcellulose, methylcellulose, and hydroxypropylcellulose, and water-soluble synthetic polymers such as polyvinyl alcohol, and polyvinylpyrrolidone.

Examples of the polyvalent isocyanate used in the aforementioned process include an adduct of trimethylolpropane and toluenediisocyanate, an adduct of trimethylolpropane and hexamethylenediisocyanate, hexamethylenediisocyanate trimer having a biuret bond, and polyvalent isocyanate having an isocyanurate structure.

Examples of the polyhydric alcohol used upon formation of a polyurethane wall include ethylene glycol, propylene glycol, butylene glycol, and cyclopropylene glycol.

Examples of the polyvalent amine used upon formation of a polyurea wall include ethylenediamine, hexamethylenediamine, diethylenetriamine, and triethylenetetramine.

Examples of the hydrophobic organic solvent which is used in the aforementioned process as necessary include aromatic hydrocarbons, and dialkyl esters of aliphatic dicarboxylic acids.

Examples of the aromatic hydrocarbon include toluene, xylene, alkylbenzene, alkylnaphthalene, and phenylxylylethane, or a mixture thereof may also be used. As the aromatic hydrocarbon, commercially available solvents may be used as they are, and examples of such the commercially available solvents include Hisol SAS-296 (mixture of 1-phenyl-1-xylylethane and 1-phenyl-1-ethylphenylethane; trade name of NIPPON OIL CORPORATION), Cactus Solvent HP-MN (methylnaphthalene 80%; trade name of JAPAN ENERGY CORPORATION), Cactus Solvent HP-DMN (dimethylnaphthalene 80%; trade name of JAPAN ENERGY CORPORATION), Cactus Solvent P-100 (alkylbenzene having 9 to 10 carbon atoms; trade name of JAPAN ENERGY CORPORATION), Cactus Solvent P-150 (alkylbenzene; trade name of JAPAN ENERGY CORPORATION), Cactus Solvent P-180 (mixture of methylnaphthalene and dimethylnaphthalene; trade name of JAPAN ENERGY CORPORATION), Cactus Solvent P-200 (mixture of methylnaphthalene and dimethylnaphthalene; trade name of JAPAN ENERGY CORPORATION), Cactus Solvent P-220 (mixture of methylnaphthalene and dimethylnaphthalene; trade name of JAPAN ENERGY CORPORATION), Cactus Solvent PAD-1 (dimethylmonoisopropylnaphthalene; trade name of JAPAN ENERGY CORPORATION), Solvesso 100 (aromatic hydrocarbon; trade name of EXXONMOBIL CORPORATION), Solvesso 150 (aromatic hydrocarbon; trade name of EXXONMOBIL CORPORATION), Solvesso 200 (aromatic hydrocarbon; trade name of EXXONMOBIL CORPORATION), Swasol 100 (toluene; trade name of MARUZEN PETEROCHEMICAL CO., LTD.), and Swasol 200 (xylene; trade name of MARUZEN PETEROCHEMICAL CO., LTD.).

Examples of the dialkyl ester of aliphatic dicarboxylic acid include dialkyl adipates such as dibutyl adipate, and dioctyl adipate. As the aliphatic dicarboxylic acid diester, commercially available solvents may be used as they are, and examples of such the commercially solvents include Vinycizer 40 (diisobutyl adipate; trade name of KAO CORPORATION) and Vinycizer 50 (diisodecyl adipate; trade name of KAO CORPORATION).

Thus, the microcapsules can be obtained as slurry containing them.

The microcapsules are used by formulating into various forms such as slurry, powder and granules. Usually, the microcapsules are used as a slurry composition in which the microcapsules are suspended in water, i.e., an aqueous suspension concentrate.

The aqueous suspension concentrate may further contain a preservative and; various stabilizers, for example, a thickener, an antifreezing agent, and a specific gravity regulating agent.

Examples of the thickener used in the aqueous suspension concentrate include natural polysaccharides such as xanthan gum, rhamsan gum, locust bean gum, carrageenan and Welan gum, synthetic polymers such as sodium polyacrylate, semisynthetic polysaccharides such as carboxymethylcellulose, mineral fine powders such as aluminum magnesium silicate, smectite, bentonite, hectorite, and silica, and alumina sol, and 0 to 10% by weight of the thickener is generally contained in the aqueous suspension concentrate. Examples of the antifreezing agent include alcohols such as propylene glycol, and 0 to 20% by weight of the antifreezing agent is generally contained in the aqueous suspension concentrate. Examples of the specific gravity regulating agent include water-soluble salts such as sodium sulfate, and water-soluble fertilizers such as urea.

The insect growth regulating active ingredient used in the insect growth regulating composition of the present invention is not particularly limited, but examples thereof include insect juvenile hormone-like compounds such as dodecadienoate compounds, oximether compounds, pyridylether compounds, and carbamate compounds, and insect chitin formation inhibiting compounds such as benzoylphenylurea compounds.

Examples of such the insect growth regulation active ingredient will be shown below together with compound numbers.

(1) Isopropyl (2E-4E)-11-methoxy-3,7,11-trimethyl-2,4-dodecadienoate <methoprene>
(2) Ethyl (2E-4E)-3,7,11-trimethyldodeca-2,4-dienoate <hydroprene>
(3) 4-phenoxyphenyl 2-(2-pyridyloxy)propyl ether <pyriproxyfen>
(4) Propionaldehyde oxime O-2-(4-phenoxyphenoxy)ethylether
(5) Propionaldehyde oxime O-2-(4-phenoxyphenoxy)propylether
(6) O-Ethyl N-[2-(4-phenoxyphenoxy)ethyl]carbamate <fenoxycarb>
(7) 1-(4-Ethylphenoxy)-6,7-epoxy-3,7-dimethyl-2-octene <R-20458>
(8) Prop-2-ynyl(±)-(E,E)-3,7,11-trimethyldodeca-2,4-dienoate <kinoprene>
(9) (E)-Z-(4-ethylphenoxy)-(2,6-dimethyl-2,3-epoxy-6-octene <ethoprene>
(9) 1-(4-Chlorophenyl)-3-(2,6-difluorobenzoyl)urea <diflubenzuron>
(10) 2-Chloro-N-[[[4-(trifluoromethoxy)-phenyl]amino]carbonyl]benzamide <triflumuron>
(11) N-[[[5-(4-bromophenyl)-6-methyl-2-pyrazinyl]amino]carbonyl]-2,6-dichlorobenzamide <EL 494>
(12) 1-(3,5-Dichloro-2,4-difluorophenyl)-3-(2,6-difluorobenzoyl)urea <teflubenzuron>
(13) 1-[3,5-Dichloro-4-(3-chloro-5-trifluoromethyl-2-pyridyloxy)phenyl]-3-(2,6-difluorobenzoyl)urea <chlorfluazuron>
(14) N-[[[3,5-dichloro-4-(1,1,2,2-tetrafluoroethoxy)phenyl]amino]carbonyl]-2,6-difluorobenzamide <XRD-473>
(15) 1-[4-(2-Chloro-α,α,α-trifluoro-p-tolyloxy)-2-fluorophenyl]-3-(2,6-difluorobenzoyl)urea <flufenoxuron>
(16) 1-[3,5-Dichloro-4-(1,1,2,2-tetrafluoroethoxy)phenyl]-3-(2,6-difluorobenzoyl)urea <hexaflumuron>
(17) (R,S)-1-[2,5-dichloro-4-(1,1,2,3,3,3-hexafluoropropoxy)phenyl]-3-(2,6-difluorobenzoyl)urea <lufenuron>
(18) (R,S)-1-[3-chloro-4-(1,1,2-trifluoro-2-trifluoromethoxyethoxy)phenyl]-3-(2,6-difluorobenzoyl)urea <novaluron>
(19) 1-(2,6-Difluorobenzoyl)-3-[2-fluoro-4-(1,1,2,2-tetrafluoroethoxy)phenyl]urea
(20) 1-(2,6-Difluorobenzoyl)-3-(2-fluoro-4-trifluoromethylphenyl)urea
(21) 2-Tert-butylimino-3-isopropyl-5-phenyl-1,3,5-thiadiazinane-4-one <buprofezin>
(22) N-cyclopropyl-1,3,5-triazine-2,4,6-triamine <cyromazine>
(23) N-tert-butyl-N'-(4-ethylbenzyl)-3,5-dimethylbenzohydrazide <tebufenozide>
(24) 2'-tert-Butyl-5-methyl-2'-(3,5-xyloyl)chroman-6-carbohydrazide <chromafenozide>
(25) N-tert-Butyl-N'-(3-methoxy-o-toluoyl)-3,5-xylohydrazide <methoxyfenozide>
(26) N-tert-Butyl-N'-(4-chlorobenzoyl)benzohydrazide <halofenozide>

Usually, 0.5 to 50% by weight of the insect growth regulating active ingredient is contained in the insect growth regulating composition of the present invention.

Then, an average particle diameter, a wall thickness, and a volume ratio of microencapsulated particles having a particle diameter of not less than 50 μm based on a total volume of microcapsules in the present invention will be explained. The average particle diameter in the present invention means a volume median diameter and, for example, a value measured using a laser diffraction type particle size analyzer (specifically, for example, Mastersizer 2000 (product of MALVERN Instruments Ltd.)) can be adopted.

The wall thickness of microcapsules varies depending on a ratio of volumes of a core substance and a wall substance, and can be calculated by the following approximate equation. That is, when Wc represents a weight of a core substance of the microcapsules, Ww represents a weight of a wall substance, ρw represents a density of a wall substance, ρc represents a density of a core substance, and d represents an average particle diameter of a core substance, the wall thickness is:

$$\text{Wall thickness} = (Ww/Wc) \times (\rho c/\rho w) \times (d/6)$$

The wall thickness referred in the present invention is calculated using this equation.

The volume ratio of microencapsulated particles having a particle diameter of not less than 50 µm based on a total volume of microcapsules can be calculated from a volume distribution measured using, for example, a laser diffraction type particle size analyzer (specifically, for example, Mastersizer 2000 (product of MALVERN Instruments Ltd.)).

In the insect growth regulating composition of the present invention, the average particle diameter is 1 to 40 µm, the wall thickness is 0.005 to 0.5 µm, the ratio of wall thickness/average particle diameter is 0.0003 to 0.003, and the volume ratio of microcapsule particles having a particle diameter of not less than 50 µm is not more than 20% by volume based on a total volume of microencapsulated particles.

In the present invention, microcapsules having an average particle diameter of 1 to 40 µm, a wall thickness of 0.005 to 0.5 µm, a ratio of wall thickness/average particle diameter of 0.0003 to 0.003, and a volume ratio of microencapsulated particles having a particle diameter of not less than 50 µm of not more than 20% by volume based on a total volume of microencapsulated particles can be obtained, for example, by adjusting (1) a kind and a concentration of a dispersant dissolved in an aqueous phase, (2) a ratio of an aqueous phase and an oil phase, and/or (3) a dispersion manner, and a stirring intense at the time of dispersing the oil phase in the aqueous phase, in the aforementioned dispersing step of the production process of the insect growth regulating composition of the present invention.

Specifically, for example, a kind and a concentration of a dispersant to be dissolved in an aqueous phase are determined, an oil phase is mixed with an aqueous phase at a volume ratio of 0.3 to 2 of the oil phase relative to 1 of the aqueous phase, and the oil phase is dispersed in the aqueous phase under appropriate operation conditions of a dispersing machine. An average particle diameter of oil particles and a volume ratio of oil particles having a particle diameter of not less than 50 µm based on a total volume of oil particles in the resulting dispersion are measured using a laser diffraction type particle size analyzer (specifically, for example, Mastersizer 2000 (product of MALVERN Instruments Ltd.)).

If the average particle diameter of oil particles in the dispersion thus obtained is less than 1 µm, a dispersion having a larger average particle diameter of oil particles can be obtained by modifying the dispersing step, such as by reducing the dispersant concentration, reducing the stirring intense at the time of dispersion of the oil phase in the aqueous phase, reducing the volume ratio of the oil phase relative to the aqueous phase, and/or changing the dispersant. On the other hand, if the average particle diameter of oil particles in the resulting dispersion is larger than 40 µm, a dispersion having a smaller average particle diameter of oil particles can be obtained by modifying the dispersing step, such as by increasing the dispersant concentration, increasing the stirring intense at the time of dispersion of the oil phase in the aqueous phase, increasing the volume ratio of the oil phase relative to the aqueous phase, and/or changing the dispersant.

If the volume ratio of oil particles having a particle diameter of not less than 50 µm based on a total volume of oil particles in the dispersion thus obtained is more than 20% by volume, a dispersion having not more than 20% by volume of the volume ratio of oil particles having a particle diameter of not less than 50 µm based on a total volume of oil particles can be obtained by modifying the dispersing step, such as by increasing the stirring speed of the dispersing machine, uniformly dispersing the entire dispersion, and/or changing the dispersant.

The properties of a particle diameter of oil particles in a dispersion are reflected in the properties of the microencapsulated particles of the microencapsulated composition obtained by the microencapsulating step.

Further, the wall thickness can be changed by adjusting amounts of the wall materials of microcapsules used for preparation of the insect growth regulating composition of the present invention, that is, the amounts of a polyvalent isocyanate and a polyhydric alcohol or a polyvalent amine, in particular, an amount of a polyvalent isocyanate according to an average particle diameter of oil particles in a dispersion. Namely, first, the conditions of the dispersing step are determined so that an average particle diameter of oil particles in a dispersion becomes 1 to 40 µm, and a volume ratio of oil particles having a particle diameter of not less than 50 µm based on a total volume of oil particles becomes not more than 20% by volume. After that, the amounts of a polyvalent isocyanate and a polyhydric alcohol or a polyvalent amine suitable for a predetermined wall thickness can be determined so that a ratio of wall thickness/average particle diameter becomes 0.0003 to 0.003.

Examples of insects on which the insect growth regulating composition of the present invention exerts efficacy include as follows.

Hemiptera insect pests: planthoppers such as *Laodelphax striatellus*, *Nilaparvata lugens*, and *Sogatella furcifera*, leafhoppers such as *Nephotettix cincticeps*, and *Nephotettix virescens*, aphids such as *Aphis gossypii*, *Myzus persicae*, *Aphis citricola*, *Lipaphis pserudobrassicae*, *Nippolachnus piri*, *Toxoptera aurantii*, and *Toxoptera ciidius*, stink bugs such as *Nezara antennata*, *Cletus punctiger*, *Riptortus clavetus*, and *Plautia stali*, whiteflies such as *Trialeurodes vaporariorum*, *Bemisia tabaci*, and *Bemisia argentifolii*, scales such as *Aonidiella aurantii*, *Comstockaspis perniciosa*, *Unaspis citri*, *Pseudaulacaspis pentagona*, *Saissatie oleae*, *Lepidosaphes beckii*, *Ceroplastes rubens*, and *Icerya purchasi*, lace bugs, and psyllids.

Lepidoptera insect pests: pyralid moths such as *Chilo suppressalis*, *Cnaphalocrocis medinalis*, *Ostrinia nubilalis*, *Hellulla undalis*, *Parapediasia terrella*, *Notarcha derogata*, and *Plodia interpunctella*, noctuid moths such as *Spodoptera litura*, *Pseudaletia separata*, *Mamestra brassicae*, *Agrotis ipsilon*, *Thoricoplusia* spp., *Heliothis* spp., and *Helicoverpa* spp., whites and sulfer butterflies such as *Pieris rapae*, tortricid moths such as *Adoxophyes* spp., *Grapholita molesta*, and *Cydia pomonolla*, Carposimidae such as *Carposina niponensis*, lyonetiid moths such as *Lyonetia* spp., tussock moths such as Lymantriidae, and *Euproctis* spp., Yponomeutidae such as *Plutella xylostella*, Gelechiidae such as *Pectinophora gossypiella*, Arctiidae such as *Hyphantria cunea*, and Tineidae such as *Tinea translucens*, and *Tineola bisselliella*.

Diptera insect pests: mosquitoes such as *Culex pipiens pallens*, and *Culex tritaeniorhynchus*, *Aedes* spp. such as *Aedes aegypti*, and *Aedes albopictus*, *Anopheles* spp. such as

*Anopheles sinensis*, midges, house flies such as *Musca domestica*, and *Muscina stabulans*, Calliphoridae, Sarcophagidae, anthomyiid flies such as lesser housefly, *Delia platura*, and *Delia antiqua*, clam flies such as *Liriomyza trifolii*, fruit flies, flea flies, small fruit flies, moth flies, Tabanidae, black flies, and stable flies.

Coleoptera insect pests: corn rootworm such as *Diabrotica virgifera*, and *Diabrotica undecimpunctata* howardi, scarabas such as *Anomala cuprea*, and *Anomala rufocuprea*, weevils such as *Sitophilus zeamais, Lissorhoptrus oryzophilus, Hypera pastica*, and *Callosobruchuys chienensis*, darkling beetles such as *Tenebrio molitor*, and *Tribolium castaneum*, leaf beetles such as *Aulacophora femoralis, Phyllotreta striolata*, and *Leptinotarsa decemlineata, Epilachna* spp. such as *Epilachna vigintioctopunctata*, false powderpost beetles, *Paederus fuscipes*.

Thysanoptera insect pests: *Thrips palmi, Thrips tabaci, Thrips hawaiiensis, Scirtothrips dorsalis, Franklinie llaintonsa, Frankliniella occidentalis*, and *Ponticulothrips diospyrosi*.

Hymenoptera insect pests: ants, Vespidae, Bethylidae, and Tenthredimidae such as *Athalia japonica*.

Orthoptera insect pests: mole crickets, and grasshoppers.

Aphaniptera insect pests: *Ctenocephalides felis, Ctenocephalides canis*, and *Pulex irritans*.

The insect growth regulating composition of the present invention is particularly effective for controlling, inter alia, scales, whiteflies, psyllids, tortricid moths, and Carposimidae.

When the insect growth regulating composition of the present invention is used for controlling insect pests, for example, the insect growth regulating composition of the present invention having a concentration of an insect growth regulation active ingredient of 0.001 to 10,000 ppm is applied by scattering directly to insect pests or plant and/or soil on which insect pests can inhabit, at a ratio of about 0.1 to 1,000 g/1,000 m², preferably about 1 to 100 g/1,000 m² as an amount of an insect growth regulation active ingredient.

That is, the insect growth regulating composition of the present invention is used in an insect pest controlling method of applying an effective amount of the insect growth regulating composition of the present invention directly to an insect pest or to a place where an insect pest inhabits.

The present invention will be explained in more detail below by way of Preparation Examples and Test Examples, but the present invention is not limited to these examples.

Preparation Example 1

An oil phase was prepared by mixing 96.6 g of pyriproxyfen, 100 g of Hisol SAS-296 (a mixture of 1-phenyl-1-xylylethane and 1-phenyl-1-ethylphenylethane; manufactured by NIPPON OIL CORPORATION), and 50 g of Vinycizer 40 (diisobutyl adipate; manufactured by KAO CORPORATION) and adding 2.4 g of Sumidur N-3300 (isocyanurate type polyvalent isocyanate; manufactured by SUMIKA BAYER URETHANE CO., LTD.) thereto.

On the other hand, an aqueous phase was prepared by mixing 17.5 g of gum arabic, 40 g of ethylene glycol, and 344.4 g of ion-exchanged water.

The oil phase and the aqueous phase were mixed, and this mixture was dispersed at room temperature for 5 minutes with T.K. Autohomomixer (homogenizer manufactured by TOKUSHU KIKA KOGYO CO., LTD.; number of revolution: about 6,100 rpm). Then, the dispersion was mildly stirred at 75° C. for 48 hours to obtain microcapsule slurry. The microcapsules in the resulting microcapsule slurry had an average particle diameter of 19.5 μm, a wall thickness of 0.031 μm, a ratio of wall thickness/average particle diameter of 0.0016, and a volume ratio of microencapsulated particles having a particle diameter of not less than 50 μm based on a total volume of microencapsulated particles of 1.3% by volume.

Then, the aforementioned microcapsule slurry was mixed with a thickener solution obtained by mixing 1.5 g of xanthan gum, 3 g of aluminum magnesium silicate, 50 g of propylene glycol and 292.5 g of ion-exchanged water to obtain the insect growth regulating composition of the present invention containing 9.7% by weight of pyriproxyfen (average particle diameter: 19.5 μm, wall thickness: 0.031 μm, wall thickness/average particle diameter: 0.0016, volume ratio of microencapsulated particles having particle diameter of not less than 50 μm based on total volume of microencapsulated particles: 1.3% by volume).

Preparation Example 2

The insect growth regulating composition of the present invention was obtained according to the same manner as that of Preparation Example 1, except that 0.96 g of Sumidur N-3300 was used, a number of revolution of T.K. Autohomomixer (homogenizer manufactured by TOKUSHU KIKA KOGYO CO., LTD.) at dispersion was about 5,000 rpm, and a thickener solution mixed with the microcapsule slurry was a mixture of 1.5 g of xanthan gum, 3 g of aluminum magnesium silicate, 50 g of propylene glycol and 293.5 g of ion-exchanged water (average particle diameter: 28.8 μm, wall thickness: 0.018 μm, wall thickness/average particle diameter: 0.0006, volume ratio of microencapsulated particles having particle diameter of not less than 50 μm based on total volume of microencapsulated particles: 11.4% by volume).

Preparation Example 3

The insect growth regulating composition of the present invention was obtained according to the same manner as that of Preparation Example 1 except that 3.36 g of Sumidur N-3300 was used, a number of revolution of T.K. Autohomomixer (homogenizer manufactured by TOKUSHU KIKA KOGYO CO., LTD.) at dispersion was about 6,100 rpm, and a thickener solution mixed with a microcapsule slurry was a mixture of 1.5 g of xanthan gum, 3 g of aluminum magnesium silicate, 50 g of propylene glycol and 291.5 g of ion-exchanged water (average particle diameter: 17.3 μm, wall thickness: 0.038 μm, wall thickness/average particle diameter: 0.0022, volume ratio of microencapsulated particles having particle diameter of not less than 50 μm based on total volume of microencapsulated particles: 0.8% by volume)

Preparation Example 4

An oil phase was prepared by mixing 96.6 g of pyriproxyfen, and 150 g of Vinycizer 40 (diisobutyl adipate; manufactured by KAO CORPORATION), and adding 1.0 g of Sumidur L-75 (adduct of trimethylolpropane and toluenediisocyanate; manufactured by SUMIKA BAYER URETHANE CO., LTD.) thereto.

On the other hand, an aqueous phase was prepared by mixing 17.5 g of gum arabic, 40 g of ethylene glycol, and 344.4 g of ion-exchanged water.

The oil phase and the aqueous phase were mixed, and this mixture was dispersed at room temperature for 5 minutes with T.K. Autohomomixer (homogenizer manufactured by TOKUSHU KIKA KOGYO CO., LTD; number of revolution: about 4,800 rpm). Then, the dispersion was mildly stirred at 75° C. for 48 hours to obtain microcapsule slurry. The microcapsules in the resulting microcapsule slurry had an average particle diameter of 33 µm, a wall thickness was 0.012 µm, a wall thickness/an average particle diameter was 0.00036, and a volume ratio of microencapsulated particles having a particle diameter of not less than 50 µm based on a total volume of microencapsulated particles was 17.6% by volume.

Then, a thickener solution obtained by mixing 1.5 g of xanthan gum, 3 g of aluminum magnesium silicate, 50 g of propylene glycol and 292.5 g of ion-exchanged water, and the microcapsule slurry were mixed to obtain the insect growth regulating composition of the present invention containing 9.7% by weight of pyriproxyfen (average particle diameter: 33 µm, wall thickness: 0.012 µm, wall thickness/average particle diameter: 0.00036, volume ratio of microencapsulated particles having particle diameter of not less than 50 µm based on total volume of microencapsulated particles: 17.6% by volume).

Reference Preparation Example

An oil phase was prepared by mixing 96.6 g of pyriproxyfen, 100 g of Hisol SAS-296 (mixture of 1-phenyl-1-xylylethane and 1-phenyl-1-ethylphenylethane; manufactured by NIPPON OIL COMPANY), and 50 g of Vinycizer 40 (diisobutyl adipate; manufactured by KAO CORPORATION), and adding 1.0 g of Sumidur L-75 (adduct of trimethylolpropane and toluenediisocyanate; SUMIKA BYEL URETHANE CO., LTD.) thereto.

On the other hand, an aqueous phase was prepared by mixing 17.5 g of gum arabic, 40 g of ethylene glycol, and 344.4 g of ion-exchanged water.

The oil phase and the aqueous phase were mixed, and this mixture was dispersed at room temperature for 5 minutes with a T.K. Autohomomixer (homogenizer manufactured by TOKUSHU KIKA KOGYO CO., LTD.; number of revolution: about 4,300 rpm). Then, the dispersion was mildly stirred at 75° C. for 48 hours to obtain microcapsule slurry. The microcapsules in the obtained microcapsule slurry had an average particle diameter of 39.5 µm, a wall thickness of 0.014 µm, a wall thickness/an average particle diameter of 0.00035, and a volume ratio of microencapsulated particles having a particle diameter of not less than 50 µm based on a total volume of microencapsulated particles of 30.2% by volume.

Then, a thickener solution obtained by mixing 1.5 g of xanthan gum, 3 g of aluminum magnesium silicate, 50 g of propylene glycol and 293.5 g of ion-exchanged water, and the microcapsule slurry were mixed to obtain an insect growth regulating composition containing 9.7% by weight of pyriproxyfen (average particle diameter: 39.5 µm, wall thickness: 0.014 µm, wall thickness/average particle diameter: 0.0004, volume ratio of microencapsulated particles having particle diameter of not less than 50 µm based on total volume of microencapsulated particles: 30.2% by volume).

Then, efficacy of the insect growth regulating composition of the present invention will be shown by Test Examples.

Test Example 1

An insect growth regulating composition to be tested was diluted with water so that a pyriproxyfen concentration became 1 ppm to prepare a test solution. A pumpkin (fruit) was immersed into the test solution for 30 seconds, and air-dried. Egg masses (200 to 300 eggs) of *Pseudaulacaspis pentagons* were placed on two sites of this pumpkin, and allowed to develop in a room at 25° C. for 25 days. Thereafter, the number of male cocoons (male prepupae) of *Pseudaulacaspis pentagons* produced on the test pumpkin was counted.

A pumpkin which had not treated with a drug was subjected to the similar test and, by taking the number of male cocoons of *Pseudaulacaspis pentagons* produced on the non-treated pumpkin as 100, a ratio of the number of male cocoons of *Pseudaulacaspis pentagona* produced on the treated pumpkin was calculated to obtain insecticidal effect. The results are shown in Table 1.

TABLE 1

|  | Insecticidal effect |
| --- | --- |
| Preparation Example 1 | A |
| Preparation Example 4 | A |
| Reference Preparation Example | C |

In Table, the insecticidal effect is represented by the following criteria:
A: The number of male cocoons of the treated pumpkin is less than 40% of the number of male cocoons of the non-treated pumpkin.
B: The number of male cocoons of the treated pumpkin is 40 to 50% of the number of male cocoons of the non-treated pumpkin.
C: The number of male cocoons of the treated pumpkin is more than 50% of the number of male cocoons of the non-treated pumpkin.

Test Example 2

A cabbage seedling planted in a plastic cup was placed for 24 hours into a net cage in which a number of *Bemisia argentifolii* inhabited, and *Bemisia argentifolii* was allowed to lay eggs on the cabbage seedling. Thereafter, the cabbage seedling was removed from the net cage, and one leaf of cabbage was taken by cutting.

On the other hand, an insect growth regulating composition to be tested was diluted with water so that a pyriproxyfen concentration became 1 ppm to prepare a test solution. The leaf of cabbage was immersed into the test solution for 30 seconds, air-dried, and allowed to develop in a room at 25° C. for 8 days. Thereafter, the numbers of hatched eggs and unhatched eggs were investigated, and an ovicidal rate was calculated. Each of the insect growth regulating compositions of the present invention prepared in Preparation Examples 1 to 4 had an ovicidal rate of 90% or higher.

As described hereinabove, the insect growth regulating composition of the present invention is useful for controlling insect pests.

What is claimed is:
1. A method for controlling an insect pest comprising scattering an effective amount of an insect growth regulating composition directly to an insect pest or to a place where an insect pest inhabits, wherein the insect growth regulating composition is a microencapsulated insect growth regulating composition, which comprises an insect growth regulating active ingredient encapsulated in a wall formed of polyurethane, having an average particle diameter of 1 to 40 µm, a wall thickness of 0.005 to 0.5 µm, and a ratio of a wall thickness/an average particle diameter of 0.0003 to 0.003, wherein a volume ratio of microencapsulated particles having a particle diameter of not less than 50 µm is not more than

20% by volume based on a total volume of microencapsulated particles, and wherein the insect pest is one in agricultural fields.

2. The method for controlling an insect pest according to claim 1, wherein the insect growth regulating active ingredient is an insect juvenile hormone-like compound.

3. The method for controlling an insect pest according to claim 1, wherein the insect growth regulating active ingredient is 4-phenoxyphenyl 2-(2-pyridyloxy)propyl ether.

* * * * *